(12) United States Patent
Osterholt et al.

(10) Patent No.: US 7,652,180 B2
(45) Date of Patent: Jan. 26, 2010

(54) PROCESS FOR PREPARING ALKYL CHLORIDES

(75) Inventors: Clemens Osterholt, Dorsten (DE);
Manfred Neumann, Marl (DE);
Thomas Kuebelbaeck, Duelmen (DE);
Kerstin Bodmann, Baltschieder (CH)

(73) Assignee: Degussa AG, Duesseldorf (DE)

( * ) Notice: Subject to any disclaimer, the term of this patent is extended or adjusted under 35 U.S.C. 154(b) by 702 days.

(21) Appl. No.: 11/359,696

(22) Filed: Feb. 23, 2006

(65) Prior Publication Data

US 2006/0205987 A1  Sep. 14, 2006

(30) Foreign Application Priority Data

Feb. 23, 2005 (DE) ............... 10 2005 008 547

(51) Int. Cl.
  *C07C 17/00* (2006.01)
(52) U.S. Cl. .......................................... 570/258
(58) Field of Classification Search ............ 570/258
  See application file for complete search history.

(56) References Cited

U.S. PATENT DOCUMENTS

| | | | |
|---|---|---|---|
| 5,767,330 A | 6/1998 | Metz et al. | |
| 5,770,780 A | 6/1998 | Metz et al. | |
| 5,831,137 A | 11/1998 | Metz et al. | |
| 6,093,286 A | 7/2000 | Osterholt et al. | |
| 6,756,513 B2 | 6/2004 | Neumann et al. | |

FOREIGN PATENT DOCUMENTS

| | | |
|---|---|---|
| CN | 1440958 A | 9/2003 |
| DE | 101 58 376 | 6/2003 |
| DE | 102 47 497 | 4/2004 |
| EP | 0 789 013 | 8/1997 |
| JP | 53-15303 | 2/1978 |
| WO | WO 2005/026089 A2 | 3/2005 |

OTHER PUBLICATIONS

Derwent-Abstract to JP 53-015303.
Synthesis (1988), 11, pp. 868-871, Branko Jursic "Organic Synthesis in Micellar Media. Oxidation of Alcohols and Their conversion into Alkyl Chlorides".
"Ionic Liquids in synthesis" (P. Wasserscheid, Wiley-VCH 2003) pp. 9-12.
Hai-Hong Wu, et al., "Immobilization of HX: [Hmim]X as Halogenating Agent, Recyclable Catalyst and Medium for Conversion of Alcohols to Alkyl Halides", Chinese Journal of Chemistry, 22, XP-008064950, 2004, pp. 619-621.

*Primary Examiner*—Jafar Parsa
(74) *Attorney, Agent, or Firm*—Oblon, Spivak, McClelland, Maier & Neustadt, L.L.P.

(57) ABSTRACT

The invention relates to a process for preparing alkyl chlorides by reacting alcohols with gaseous hydrogen chloride in the presence of a catalyst, wherein the catalyst comprises at least one compound of the structure:

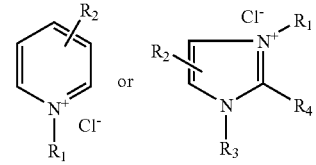

wherein
  $R_1$ is a linear alkyl group having from 1 to 20 carbon atoms,
  $R_2$, $R_3$, and $R_4$ is selected from a hydrogen, an alkyl, an alkenyl, an aralkyl or an alkylaryl group from 1 to 20 carbon atoms, wherein the substituents of $R_2$, $R_3$, and $R_4$ are all identical, are all different or two of the substituents of $R_2$, $R_3$, and $R_4$ type are identical.

14 Claims, No Drawings

PROCESS FOR PREPARING ALKYL CHLORIDES

FIELD OF THE INVENTION

The present invention relates to a process for preparing alkyl chlorides by reacting the corresponding alcohols with gaseous hydrogen chloride in the presence of a catalyst.

BACKGROUND OF THE INVENTION

Acyclic chlorohydrocarbon can be prepared by reacting corresponding alcohols with hydrogen chloride ("Traité de Chimie organique" by Grignard and Baud, (Paris 1935, Volume III, page 249). This reaction can be carried out using a catalyst, such as Lewis acids. In addition to Lewis acids, examples of suitable catalysts include iron chloride, aluminum chloride, arsenic chloride, antimony chloride, tin chloride, and zinc chloride. Other suitable catalysts include amine hydrohalides, in particular amine hydrobromides and amine hydrochlorides. For example, such catalysts include primary, secondary, or tertiary amines with unbranched or branched, acyclic or cyclic carbon chains, or amines having aromatic groups. In particular, they may also be heteroaromatic amines, for example, alkylpyridines. EP 0 789 013, DE 101 58 376, and DE 102 47 497 describe a continuous process for preparing alkyl chlorides by reacting alcohols with hydrogen chloride in the presence of a catalyst, for example, an aqueous alkylpyridine hydrochloride solution.

The Derwent Abstract for JP 53-015303 describes the preparation of alkyl halides by reacting alcohols that have at least 4 carbon atoms with an aqueous solution of hydrogen halide in the presence of quaternary ammonium compounds as a catalyst. JP 53-015303 describes a method for the preparation of stearylpyridinium bromide catalyst, which involves stirring together a mixture of 1 mol of stearyl bromide and 1 mol of pyridine at a temperature range from 80° C. to 100° C. for 5 hours. To prepare lauryl chloride, a mixture of lauryl alcohol and concentrated hydrochloric acid can be heated at an elevated temperature for 24 hours. In Synthesis 11 (1988), 868-871, Jursic describes the reaction of primary alcohols with aqueous hydrochloric acid in the presence of micelles (as phase mediators), such as hexadecyltrimethylammonium bromide and hexadecylpyridinium bromide (cetylpyridinium bromide). The alkyl chlorides produced by such method can be isolated by following a complicated extraction step with petroleum ether, a filtration through silica gel, and a subsequent distillation under reduced pressure. For example, octyl chloride can be obtained with a purity of 96%.

SUMMARY OF THE INVENTION

In various embodiments, the processes of the present invention for preparing alkyl chloride provide a number of advantages that are lacking in the prior art processes. In one embodiment, the present invention provides an optimized industrial process for preparing alkyl chlorides, which includes features such as short reaction times, high space-time yields, and also high conversions based on the type of alcohol used. In particular, as one embodiment, the present invention simplifies the process for the workup, the purification, and the storage of the catalyst when compared to the prior art processes. In various embodiments, the processes of the present invention utilize compounds of structure I as catalysts in reactions of gaseous hydrogen chloride with alcohols and/or diols. In such reactions, the reaction surprisingly proceeds with distinctly shorter reaction times at a high conversion based on the type of alcohol used, when compared to processes that utilize pyridinium hydrochloride as a catalyst.

DETAILED DESCRIPTION OF THE INVENTION

The process of the present invention enables a process for preparing alkyl chlorides with high space-time yields. The process of the present invention can advantageously be used for the preparation of the alkyl chlorides that can be implemented in common industrial plants. For example, unlike processes that utilize alkylpyridine hydrochloride as a catalyst and that requires the use an aqueous solution of the catalyst and heated plant components, the process of the present invention does not require an aqueous solution of the catalyst nor heated plant components because the melting point of the catalyst is lower than that of conventional catalysts.

A particular advantage of the process of the present invention is that it enables the selection of a catalyst which can be made independently without regard to the type of alcohol selected as a reagent. According to the present invention, the alkyl group on the nitrogen atom of the catalyst is sufficiently stable in the process so that the alkyl group $R_1$ on the nitrogen atom in structure I does not have to be identical to the alkyl group of the alcohol or the alkyl chloride prepared. Thus, a single type of catalyst can be used for the preparation of different alkyl chlorides.

In another embodiment, the process of the present invention reduces the amount of wastewater produced because unlike processes that require aqueous hydrochloric acid, the process of the present invention utilizes gaseous hydrogen chloride. Furthermore, by reacting together the catalysts of structure I with chloride anions instead of bromide anions, the risk for producing alkyl bromides in addition to the desired alkyl chlorides can be reduced and/or eliminated.

In one embodiment, the process of the present invention is suitable for preparing alkyl chlorides having from 3 to 20 carbon atoms. In another embodiment, the process of the present invention is suitable for preparing alkyl chlorides having from 4 to 14 carbon atoms. In another embodiment, the process of the present invention is suitable for preparing alkyl chlorides having from 4 to 8 carbon atoms. In the context of the present invention, the term alkyl chlorides means both monochloroalkanes and dichloroalkanes, including $\alpha,\omega$-dichloroalkanes. In one embodiment, the process of the present invention produces dichloroalkanes having from 3 to 20 carbon atoms. In another embodiment, the process of the present invention produces dichloroalkanes having from 4 to 12 carbon atoms. In another embodiment, the process of the present invention produces dichloroalkanes having from 4 to 8 carbon atoms.

Embodiments of the present invention provide processes for preparing alkyl chlorides by reacting various alcohols with gaseous hydrogen chloride in the presence of a catalyst, wherein the catalyst comprises at least one compound of the structure I provided below:

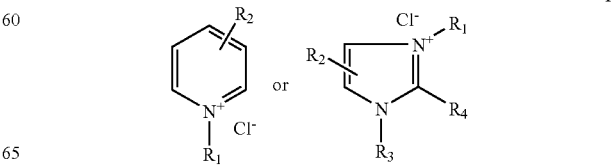

in which $R_1$ is a linear alkyl group having from 1 to 20 carbon atoms; $R_2$, $R_3$, and $R_4$ are each selected from a hydrogen, an alkyl, an alkenyl, an aralkyl, or an alkylaryl group having from 1 to 20 carbon atoms, wherein the substituents of $R_2$, $R_3$, and $R_4$ are all identical, are all different, or two of these substituents of $R_2$, $R_3$, and $R_4$ are identical.

In one embodiment, a suitable catalyst comprises at least one compound of structure I having a melting point not exceeding 100° C. In another embodiment, a suitable catalyst comprises ionic liquids that include salts of the compounds of structure I that have a melting point not more than 100° C.

In one embodiment, the process of the present invention utilizes a catalyst that comprises at least one compound of structure II provided below:

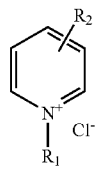

II in which $R_1$ is a linear alkyl group having from 1 to 20 carbon atoms, $R_2$ is selected from a hydrogen, an alkyl, an alkenyl, an aralkyl, or an alkylaryl group having from 1 to 20 carbon atoms.

In the context of the present invention, an alkylaryl group means an aryl group substituted by alkyl groups, for example $H_3C-CH_2-C_6H_4-$, and an aralkyl group means an alkyl group substituted by aryl groups, for example $H_5C_6-CH_2-CH_2-$.

In one embodiment, the process of the present invention utilizes a catalyst having at least one compound of structure II, wherein the substituent of $R_1$ has from 2 to 13 carbon atoms. In another embodiment, the process of the present invention utilizes a catalyst having at least one compound of structure II, wherein the substituent of $R_1$ has from 3 to 8 carbon atoms.

In one embodiment, the process of the present invention utilizes a catalyst comprising at least one compound of structure II that has an n-butyl or an n-octyl group, and in particular an n-butyl group, as a substituent of $R_1$. In another preferred embodiment, the process of the present invention utilizes catalysts comprising a compound of structure II that has an alkyl group as a substituent of $R_2$. In another embodiment, the alkyl group has from 1 to 8 carbon atoms. In another preferred embodiment, the alkyl group has from 2 to 4 carbon atoms.

In one embodiment, a catalyst suitable for the process of the present invention comprises N-n-butylalkylpyridinium chloride of structure III, provided below, having a substituent of $R_2$ selected from a hydrogen, a methyl group, and an ethyl group:

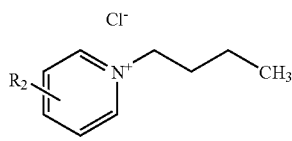

III

In another embodiment, a catalyst suitable for the process of the present invention comprises N-n-octylalkylpyridinium chloride of structure IV, provided below, having a substituent of $R_2$ selected from a hydrogen, a methyl group, and an ethyl group:

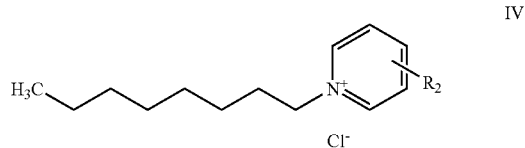

IV

In a further embodiment, a catalyst suitable for the process of the present invention comprises at least one compound of structure V provided below:

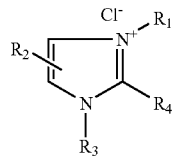

V $R_1$ is a linear alkyl group having from 1 to 20 carbon atoms; $R_2$, $R_3$, and $R_4$ are each selected from a hydrogen, an alkyl, an alkenyl, an aralkyl, or an alkylaryl group having from 1 to 20 carbon atoms, wherein the substituents of $R_2$, $R_3$, and $R_4$ are all identical, are all different or two of these substituents of $R_2$, $R_3$, and $R_4$ are identical.

In another embodiment, a catalyst suitable for the process of the present invention comprises at least one compound of the structure V, in which the substituent of $R_1$ comprises an alkyl group having from 2 to 13 carbon atoms. In another embodiment, a catalyst suitable for the process of the present invention comprises at least one compound of the structure V, in which the substituent of $R_1$ comprises an alkyl group having from 3 to 8 carbon atoms. In another embodiment, a catalyst suitable for the process of the present invention comprises at least one compound of the structure V, in which the substituent of $R_1$ comprises an n-butyl group or an n-octyl group. In another embodiment, a catalyst suitable for the process of the present invention comprises at least one compound of structure V, in which the substituents of $R_2$, $R_3$, and $R_4$ are each selected from an alkyl group having from 1 to 8 carbon atoms. In another embodiment, a catalyst suitable for the process of the present invention comprises at least one compound of structure V, in which the substituents of $R_2$, $R_3$, and $R_4$ are each selected from an alkyl group having from 2 to 4 carbon atoms.

In another embodiment, a catalyst suitable for the process of the present invention comprises at least one compound based on 1-alkyl-3-alkylimidazolium chlorides of structure VI provided below:

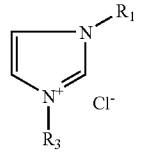

VI in which, $R_1$ is a linear alkyl group having from 1 to 8 carbon atoms; $R_3$ is an alkyl group having from 1 to 8 carbon atoms.

In another embodiment, a catalyst suitable for the process of the present invention comprises 1-alkyl-3-alkylimidazolium chloride in which each of the $R_1$ and $R_3$ substituents comprises an alkyl group having from 1 to 4 carbon atoms. The two alkyl groups of $R_1$ and $R_3$ substituents may be identical or different. In another embodiment, a catalyst suitable for the process of the present invention comprises at least 1-n-butyl-3-methylimidazolium chloride.

In another embodiment, a catalyst suitable for the process of the present invention comprises a mixture of alkylated N-alkylpyridinium chlorides and/or alkylated N-alkylimidazolium chlorides, and the catalyst is prepared in a preceding process step. In another embodiment, a catalyst suitable for the process of the present invention comprises a mixture of different isomers of alkylated N-alkylpyridinium chloride and/or alkylated N-alkylimidazolium chloride.

In another embodiment, a catalyst suitable for the process of the present invention comprises a mixture of different isomers of alkylated N-alkylpyridinium chlorides. In another embodiment, a catalyst suitable for the process of the present invention comprises a mixture of different isomers of N-alkylmethylpyridinium chlorides and/or N-alkylethylpyridinium chlorides. In another embodiment, a catalyst suitable for the process of the present invention comprises a mixture comprising N-alkyl-2-methylpyridinium chloride, N-alkyl-3-methylpyridinium chloride, N-alkyl-4-methylpyridinium chloride and/or N-alkyl-2-ethylpyridinium chloride.

In another embodiment, a catalyst suitable for the process of the present invention comprises monoalkylated N-alkylpyridinium chlorides. In another embodiment, a catalyst suitable for the process of the present invention comprises a mixture comprising polyalkylated N-alkylpyridinium chlorides having a plurality of substituents of $R_2$ on the nitrogen heterocycle. In another embodiment, a catalyst suitable for the process of the present invention comprises a mixture comprising different isomers of monoalkylated and/or polyalkylated N-alkylpyridinium chlorides, in which the polyalkylated N-alkylpyridinium chloride has a plurality of substituents of $R_2$ on the nitrogen heterocycle. The mixtures used as the catalyst in the process according to the invention may, in addition to the alkylated N-alkyl-pyridinium chlorides, also comprise alkyl-pyridines and/or dialkylpyridines, including 2-methylpyridine, 3-methylpyridine, 4-methylpyridine, 2-ethylpyridine, 2,3-dimethylpyridine, 2,4-dimethylpyridine, 2,5-dimethylpyridine, and 2,6-dimethylpyridine. The catalyst suitable for the present invention may be prepared in a preceding process step.

In another embodiment, a catalyst suitable for the process of the present invention comprises N-n-butylalkylpyridinium chloride of structure III with a substituent of $R_2$ selected from a hydrogen, a methyl group, and an ethyl group. In another embodiment, a catalyst suitable for the process of the present invention comprises a mixture of different isomers of N-n-butylalkylpyridinium chloride, and this mixture may further comprise polyalkylated N-n-butylpyridinium chlorides. The polyalkylated N-n-butylalkylpyridinium chloride may have a plurality of substituents of $R_2$ on the nitrogen heterocycle.

In a preferred embodiment, the catalyst comprises at least one compound of structure V which has an n-butyl group as a substituent of the $R_1$ type.

The catalyst suitable for the process of the present invention may be purchased commercially or may be prepared in a preceding reaction by reacting together alkylpyridines, or an alkylpyridine mixture, with an alkyl chloride at a temperature range from 50° C. to 150° C., as described in "Ionic Liquids in Synthesis" (P. Wasserscheid, Wiley-VCH-Verlag, 2003, pages 9-12). Subsequently, the catalyst phase is removed and freed of dissolved alkyl chloride by steam distillation. Complicated isolation and purification of the catalyst is unnecessary. In a preferred embodiment of the process of the present invention, the catalyst is prepared in a preceding process step from a mixture of alkylpyridines and dialkylpyridines.

The catalyst suitable for the process of the present invention can be prepared in a separate process or in a preceding step of the process of the present invention. In one embodiment, a catalyst suitable for the process of the present invention is prepared in a preceding process step and can be utilized directly without further purification. In another embodiment of the process of the invention, the catalyst is prepared in situ. However, it is also possible to use commercially available compounds of structures I, II, III, IV, V, and VI as catalysts in the process of the present invention.

In one embodiment, a reactant suitable for the process of the present invention is an alcohol having one or two hydroxyl groups. In one embodiment, a reactant suitable for the process of the present invention is an alcohol having from 3 to 20 carbon atoms. In another embodiment, a reactant suitable for the process of the present invention is an alcohol having from 4 to 14 carbon atoms. In another embodiment, a reactant suitable for the process of the present invention is an alcohol having from 4 to 8 carbon atoms. In another embodiment, a reactant suitable for the process of the present invention is a linear or a branched alcohol. In another embodiment, a reactant suitable for the process of the present invention is a linear alcohol having one hydroxyl group, selected from n-propanol, n-butanol, n-hexanol, n-octanol, n-tetradecanol, and n-octadecanol. In another embodiment, a reactant suitable for the process of the present invention is a branched alcohol. In another embodiment, a reactant suitable for the process of the present invention is a branched alcohol having one hydroxyl group, preferably selected from isopropanol, isobutanol, sec-butanol, and 2-ethylhexanol. In another embodiment, a reactant suitable for the process of the present invention is a diol which is an alcohol having two hydroxyl groups. In another embodiment, a reactant suitable for the process of the present invention is $\alpha,\omega$-dihydroxyalkanes. In another embodiment, a reactant suitable for the process of the present invention is at least one diol selected from 1,6-hexanediol, 1,8-octanediol, and 1,10-decanediol.

The processes of the present invention may be implemented as a batchwise process, a semicontinuous process, or a continuous process. In one embodiment, the process of the present invention is implemented as a semicontinuous process or a continuous process. In another embodiment, the process of the present invention is implemented continuously in a reactor. In another embodiment, the process of the present invention is implemented in a plurality of reactors which are connected to one another in the form of a battery. In another embodiment, the process of the present invention is implemented in a battery having at least two reactors. For the preparation of alkyl chlorides having from 11 to 20 carbon atoms, the preferred method is a semicontinuous process.

In one embodiment, the process of the present invention produces a reaction product preferably drawn off in vapor form, without or via an attached column, and are subsequently condensed. The water formed in the reaction is preferably either removed azeotropically with the alkyl chloride formed, or directly removed by distillation. The phases that form are separated and can be subject to a separate workup. The lower aqueous phase can be freed of the organic constituents by means of a stripper column, and the lower aqueous phase may be subsequently fed back into the reaction. The upper organic phase is preferably used partly as a column reflux; the remaining amount may be extracted under alkaline conditions to remove residual alcohol, and can be dried over caustic soda. When the purity of the alkyl chloride is over 99% achieved, a distillation is not required.

In one embodiment, the process of the present invention produces a reaction product that can be removed via a laterally attached overflow. The reaction product is preferably removed by withdrawing a portion of the reaction mixture, for example, via a lateral overflow, and transferring it into a holding vessel for phase separation. The catalyst phase—the lower phase may be removed and recycled into the reaction. Depending on the type of the alkyl chloride, the upper product phase may be further processed by, for example, subsequent washing and/or distillation. Such processing steps are suitable for the preparation of relatively high-boiling or high-boiling alkyl chlorides having from 7 to 20 carbon atoms, particularly for the preparation of alkyl chlorides having from 7 to 12 carbon atoms.

In one embodiment, the process of the present invention produces a reaction product that is discharged from the reactor in a vapor form; in particular, by means of azeotrope formation with hydrochloric acid. Subsequently, the product is condensed and separated from the water of the reaction by means of a phase separation. The resulting organic phase may subsequently be worked up by means of thermal separating processes, in particular distillation. Such processing steps are suitable in the preparation of low-boiling alkyl chlorides having from 3 to 10 carbon atoms, particularly for the preparation of alkyl chlorides having from 4 to 8 carbon atoms.

In one embodiment, the process of the present invention produces an alkyl chloride product that may be removed by azeotropic distillation, and which can be recycled into the reactor after the phase separation on a water separator.

In one embodiment, the process of the present invention is implemented at a temperature of from 60° C. to 160° C. In a embodiment, for the preparation of alkyl chlorides having from 3 to 6 carbon atoms, the process of the present invention is carried out at a temperature of from 60° C. to 160° C. In another embodiment, for the preparation of alkyl chlorides having from 3 to 6 carbon atoms, the process of the present invention is carried out at a temperature from 80° C. to 150° C. In another embodiment, for the preparation of alkyl chlorides having from 7 to 10 carbon atoms, the process of the present invention is carried out at a temperature of from 110° C. to 160° C. In another embodiment, for the preparation of alkyl chlorides having from 7 to 10 carbon atoms, the process of the present invention is carried out at a temperature range from 130° C. to 150° C. In another embodiment, for the preparation of alkyl chlorides having from 11 to 20 carbon atoms, the process of the present invention is carried out at a temperature of from 100° C. to 170° C., in particular, from 140° C. to 160° C.

In one embodiment, the process of the present invention is carried out at atmospheric pressure.

It will be appreciated that, although specific embodiments of the present invention have been described herein for purposes of illustration, various modifications may be made without departing from the spirit and scope of the invention. Accordingly, the invention is not limited except as by the appended claims.

EXAMPLES

Example 1

Preparation of the N-n-Butylalkylpyridinium Chloride Catalyst 675 g of n-butyl chloride are added to 600 g of an alkylpyridine mixture and stirred at 80° C. for 70 h. The reaction mixture forms a biphasic system, with the catalyst disposed in the lower phase. The upper phase which comprises predominantly the excess n-butyl chloride is removed by phase separation. The n-Butyl chloride dissolved in the lower phase is removed by a steam distillation when the catalyst is used for the preparation of alkyl chlorides different from the n-butyl chloride.

Example 2

Preparation of the N-n-Octylalkylpyridinium Chloride Catalyst 2180 g of n-octyl chloride are added to 1031 g of an alkylpyridine mixture according to Example 1 and the mixture is stirred at 90° C. for 160 hours. The reaction mixture forms a biphasic system, the catalyst being disposed in the lower phase. The upper phase which comprises predominantly the excess n-octyl chloride is removed by means of phase separation. n-Octyl chloride dissolved in the lower phase is removed by a steam distillation when the catalyst is used for the preparation of alkyl chlorides different from n-octyl chloride.

Example 3a

Continuous Preparation of n-Butyl Chloride

A 1 l jacketed glass reactor with a glass paddle stirrer and immersed tube for reactant metering is initially charged with 290.6 g of N-n-butylalkylpyridinium chloride (prepared according to Example 1 as catalyst and adjusted to a temperature of 135° C., and 50 g of n-butanol and 38 g of gaseous hydrogen chloride per hour are metered in via the immersed tube. The reaction product obtained is removed in vapor form via a distillation apparatus and subsequently condensed. The biphasic reaction product is separated and the organic phase is worked up by known methods. After multistage washing and drying over caustic soda, butyl chloride was obtained with a purity of >99.5%.

Analysis: Phase distribution: upper organic phase: lower aqueous phase=64.7:35.3% by weight. Conversion based on n-butanol: 81%.

Comparative Example 3b

Continuous Preparation of n-Butyl Chloride

The procedure corresponds to that of Example 3a with the exception that the catalyst used is an alkylpyridine hydrochloride.

Analysis: Phase distribution: upper organic phase: lower phase=50:50% by weight. Conversion based on n-butanol: 60%.

Example 4a

Preparation of 2-Ethylhexyl Chloride in a Semicontinuous Process

A 1 l jacketed glass reactor with a glass paddle stirrer, an immersed tube for reactant metering and an attached water separator is initially charged with 200 g of N-n-butylalkylpyridinium chloride (prepared according to Example 1 as catalyst and adjusted to a temperature of 135° C. 519.8 g of 2-ethylhexanol are introduced uniformly via the immersed tube within 5 h. Over the entire reaction time, gaseous hydrogen chloride is likewise metered in via the immersed tube in a slight stoichiometric excess (223 g). The water of reaction is distilled off azeotropically with the target product and removed as the lower phase in the water separator, while the upper phase is recycled into the reactor. After a total reaction time of 22 h, the conversion based on the 2-ethylhexanol is 99.3%.

Comparative Example 4b

Preparation of 2-Ethylhexyl Chloride in a Semicontinuous Process

The procedure corresponds to that of Example 4a with the exception that the catalyst used is an alkylpyridine hydrochloride. After a total reaction time of 22 h, the conversion based on the 2-ethylhexanol is 81.9% and, after a total reaction time of 34 h, it is 93%.

Example 5a

Continuous Preparation of n-Octyl Chloride in a Battery Method

Two 1 l glass reactors connected in series are connected by a laterally attached overflow. The overflow is constructed and attached in such a way that only the upper product phase is transferred into the subsequent reactor and the lower catalyst phase remains in the reactor. Both reactors are initially charged up to the overflow with 460 g of N-n-octylalkylpyridinium chloride (prepared according to Example 2) as a catalyst and adjusted to a temperature of 135-147° C. n-Octanol and gaseous hydrogen chloride (10-50 g/h depending on n-octanol feeds) are metered continuously into the first reactor via an immersed tube. The upper organic phase of the first reactor is transferred continuously into the second reactor and gaseous hydrogen chloride (5-15 g/h) is likewise introduced continuously via an immersed tube. The water of reaction formed in the reaction is discharged in both reactors azeotropically by means of a water separator, the upper n-octyl chloride phase being recycled into the particular reactor. Hydrogen chloride is added in both reactors in a slight stoichiometric excess. Depending on the feed rates of n-octanol in the first reactor, the following conversions based on the n-octanol are achieved:

| Feed of n-octanol in the 1st reactor (in g/h) | Conversion of n-octanol in the 1st reactor (in %) | Conversion of n-octanol in the 2nd reactor (in %) |
|---|---|---|
| 26.5 | 99.3 | >99.9 |
| 43 | 98.7 | >99.9 |
| 66.4 | 97.7 | >99.9 |
| 93.7 | 95.8 | >99.8 |
| 108 | 94.6 | 99.8 |

Comparative Example 5b

Continuous Preparation of n-Octyl Chloride in a Battery Method

The procedure corresponds to that of Example 5a with the exception that the catalyst used is an alkylpyridine hydrochloride. Depending on the feed rates of n-octanol in the first reactor, the following conversions based on the n-octanol are achieved:

| Feed of n-octanol in the 1st reactor (in g/h) | Conversion of n-octanol in the 1st reactor (in %) | Conversion of n-octanol in the 2nd reactor (in %) |
|---|---|---|
| 34 | 94.8 | 99.8 |

Example 6a

Preparation of n-Tetradecyl Chloride in a Semicontinuous Process

A 1 l jacketed glass reactor with a glass paddle stirrer, an immersed tube for reactant metering and an attached water separator is initially charged with 200 g of N-n-octylalkylpyridinium chloride (prepared according to Example 2) as catalyst and adjusted to a temperature of 150° C. 243 g of n-tetradecanol are introduced uniformly via the immersed tube within 4.5 h. Over the entire reaction time, gaseous hydrogen chloride in a slight excess is metered in via the immersed tube, while the water of reaction formed is removed distillatively from the reaction mixture. The performance of the reaction and workup are analogous to Example 4a. After a total reaction time of 7.5 h, the conversion based on n-tetradecanol is 99.5%.

Comparative Example 6b

Preparation of n-Tetradecyl Chloridein a Semicontinuous Process

The procedure corresponds to Example 6a with the exception that the catalyst used is an alkylpyridine hydrochloride. After a total reaction time of 7.5 h, the conversion based on n-tetradecanol is 87.2% and, after a total reaction time of 15.5 h, it is 99.2%.

Example 7a

Preparation of n-Octadecyl Chloride in a Semicontinuous Process

A 1 l jacketed glass reactor with a glass paddle stirrer and immersed tube for reactant metering is initially charged with 220 g of N-n-octylalkylpyridinium chloride (prepared according to Example 2) and adjusted to a temperature of 150° C. 447 g of n-octadecanol are introduced uniformly via an immersed tube over 5 hours. Gaseous hydrogen chloride is metered in via an immersed tube in a slight stoichiometric excess over the entire reaction time, and the water of reaction formed is simultaneously removed via distillation. The performance of the reaction and the workup of the reaction mixture are analogous to Example 4a. After a total reaction time of 8 h (including 3 hours of postreaction), the conversion based on n-octadecanol is 99.8%.

Example 7b

Preparation of n-Octadecyl Chloride in a Semicontinuous Process

The procedure corresponds to that of Example 7a with the exception that the catalyst used is an alkylpyridine hydrochloride. After a total reaction time of 8 h, the conversion based on the n-octadecanol is 62.7% and, after a total reaction time of 39 h, it is 99.4%.

This application claims priority to DE 10 2005 008 547.4 filed Feb. 23, 2005, the entire contents of which are incorporated herein by reference.

What is claimed is:

1. A process for preparing alkyl chlorides comprising:
reacting an alcohol with gaseous hydrogen chloride in the presence of a catalyst,
wherein the catalyst comprises at least one compound of the structure:

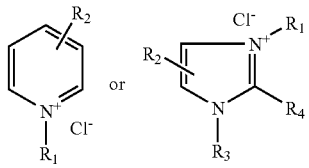

wherein $R_1$ is a linear alkyl group having from 1 to 20 carbon atoms,
wherein $R_2$, $R_3$, and $R_4$ are each selected from a hydrogen, an alkyl, an alkenyl, an aralkyl, or an alkylaryl group having from 1 to 20 carbon atoms,
wherein the substituents of $R_2$, $R_3$ and $R_4$ are all identical, are all different or two of these substituents of $R_2$, $R_3$, and $R_4$ are identical.

2. The process as claimed in claim 1,
wherein the catalyst comprises at least one compound of the structure:

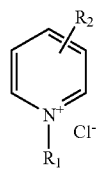

wherein $R_1$ is a linear alkyl group having from 1 to 20 carbon atoms,
wherein $R_2$ is a hydrogen, an alkyl, an alkenyl, an aralkyl, or an alkylaryl group having from 1 to 20 carbon atoms.

3. The process as claimed in claim 1,
wherein the catalyst comprises at least one compound of the structure:

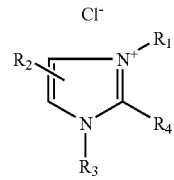

wherein $R_1$ is a linear alkyl group having from 1 to 20 carbon atoms,
wherein $R_2$, $R_3$, and $R_4$ are each selected from a hydrogen, an alkyl, an alkenyl, an aralkyl, or an alkylaryl group having from 1 to 20 carbon atoms,
wherein the substituents of $R_2$, $R_3$, and $R_4$ are all identical, are all different or two of these substituents of the $R_2$, $R_3$, and $R_4$ type are identical.

4. The process as claimed in claim 1, which is carried out continuously.

5. The process as claimed in claim 4, which is carried out in a plurality of reactors which are connected to one another in the form of a battery.

6. The process as claimed in claim 1, wherein the alcohol has from 3 to 20 carbon atoms.

7. The process as claimed in claim 6, wherein the alcohol is a linear alcohol having one hydroxyl group, selected from the group consisting of n-propanol, n-butanol, n-hexanol, n-octanol, n-tetradecanol, and n-octadecanol.

8. The process as claimed in claim 6, wherein the alcohol is a branched alcohol having one hydroxyl group, selected from the group consisting of isopropanol, isobutanol, sec-butanol, and 2-ethylhexanol.

9. The process as claimed in claim 6, wherein the alcohol has two hydroxyl groups, selected from 1,6-hexanediol, 1,8-octanediol, and 1,10-decanediol.

10. The process as claimed in claim 1, wherein the reaction product is discharged from the reactor in a vapor form.

11. The process as claimed in claim 1, wherein the reaction product is removed via a laterally attached overflow.

12. The process as claimed in claim 1, which is carried out at a temperature of from 60° C. to 160° C.

13. The process as claimed in claim 1, wherein the catalyst used is a mixture that comprises different isomers of monoalkylated and/or polyalkylated N-alkylpyridinium chlorides, wherein the polyalkylated N-alkylpyridinium chlorides have a plurality of substituents of $R_2$ on the nitrogen heterocycle.

14. The process as claimed in claim 13, wherein the catalyst is prepared in a preceding process step.

* * * * *